United States Patent [19]

Kumar et al.

US005763646A

[11] Patent Number: 5,763,646
[45] Date of Patent: Jun. 9, 1998

[54] PROCESS FOR MANUFACTURING SIMVASTATIN FROM LOVASTATIN OR MEVINOLINIC ACID

[75] Inventors: Yatendra Kumar; Rajesh Kumar Thaper, both of Haryana; Satyananda Misra, New Delhi; S. M. Dileep Kumar, New Delhi; Jag Mohan Khanna, New Delhi, all of India

[73] Assignee: Ranbaxy Laboratories, Ltd., New Delhi, India

[21] Appl. No.: 816,573

[22] Filed: Mar. 13, 1997

[51] Int. Cl.⁶ .................................................. C07C 67/02
[52] U.S. Cl. .............................................. 560/252; 549/292
[58] Field of Search ............................... 549/292; 560/252

[56] References Cited

U.S. PATENT DOCUMENTS

| | | |
|---|---|---|
| 3,983,140 | 9/1976 | Endo et al. . |
| 4,231,938 | 11/1980 | Monaghan et al. . |
| 4,293,496 | 10/1981 | Willard . |
| 4,444,784 | 4/1984 | Hoffman et al. . |
| 4,450,171 | 5/1984 | Hoffman et al. . |
| 4,582,915 | 4/1986 | Sleteinger et al. . |
| 4,584,389 | 4/1986 | Sletzinger et al. . |
| 4,611,081 | 9/1986 | Lynch et al. . |
| 4,820,850 | 4/1989 | Verhoeven et al. . |
| 5,159,104 | 10/1992 | Dabora et al. . |
| 5,223,415 | 6/1993 | Conder et al. . |
| 5,393,893 | 2/1995 | Kubela et al. . |

OTHER PUBLICATIONS

"Synthesis of Synvinolin: Extremely High Conversion Alkylation of an Ester Enolat," D. Askin, T.R. Verhoeven, T. M.H. Liu, I. Shinkai, *J. Org. Chem.*, 56, pp. 4929–4932 (1991).

*Primary Examiner*—Michael L. Shippen
*Attorney, Agent, or Firm*—Meltzer, Lippe, Goldstein, Wolf, & Schlissel, P.C.

[57] ABSTRACT

A process for preparing simvastatin from lovastatin or mevinolinic acid in salt form comprises treating either starting material with cyclopropyl or butyl amine, the pyranone ring thereby being opened when lovastatin is the starting material, adding a methyl group to the 2-methylbutyrate side chain, and thereafter closing the open pyranone ring to produce simvastatin. The process is performed without protecting and deprotecting the two hydroxy groups of the open pyranone ring. In a preferred embodiment, the starting material is treated with cyclopropyl amine which produces simvastatin via the novel intermediate lovastatin cyclopropyl amide.

23 Claims, No Drawings

PROCESS FOR MANUFACTURING SIMVASTATIN FROM LOVASTATIN OR MEVINOLINIC ACID

REFERENCE TO RELATED APPLICATION

This patent application is related to a patent application entitled "KEY INTERMEDIATES IN THE MANUFACTURE OF SIMVASTATIN" assigned Ser. No. 08/816,574, and filed on Mar. 13, 1997.

BACKGROUND OF THE INVENTION

Compounds of structure I shown below are very active antihypercholesterolenic agents that function to limit cholesterol biosynthesis by inhibiting the enzyme HMG-CoA reductase.

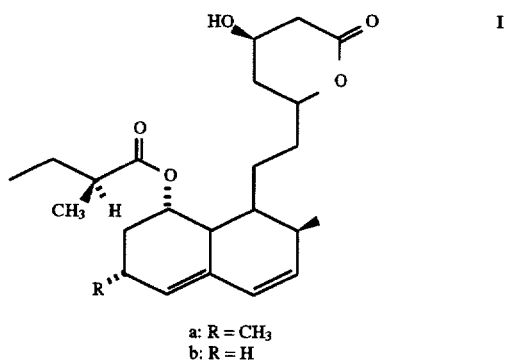

a: R = CH₃
b: R = H

Compounds of structure I include the natural fermentation products mevinolin (structure Ia where R=CH₃, disclosed in U.S. Pat. No. 4,231,938, and also known as lovastatin), compactin (structure Ib where R=H, disclosed in U.S. Pat. No. 3,983,140), and a variety of semi-synthetic and totally synthetic analogs thereof, all having the natural 2-methylbutyrate side chain.

Compounds of structure II shown below having a 2,2-dimethylbutyrate side chain (e.g., simvastatin, structure IIa where R=CH₃) are known to be more active inhibitors of HMG-CoA reductase than their 2-methylbutyrate analogs, and thus of greater utility in the treatment of atherosclerosis, hyperlipemia, familial hypercholesterolemia, and similar disorders.

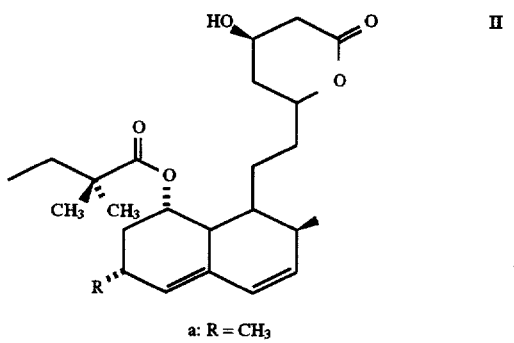

a: R = CH₃

The recent introduction into the market of simvastatin (IIa), a more potent HMG-CoA reductase inhibitor than lovastatin (Ia), has provided a need for a high yielding process which is more economically efficient and environmentally sound than those disclosed in the prior art.

Compounds of structure II (e.g., simvastatin) with the 2,2-dimethylbutyrate side chain, and processes for their preparation are disclosed in U.S. Pat. No. 4,444,784 and EPO published patent application No. 33538. The process disclosed therein involves four distinct chemical steps:

(1) de-esterification of the 2-methylbutyrate side chain;

(2) protection of the 4-hydroxy group of the pyranone ring;

(3) re-esterification of the side chain to form the desired 2,2-dimethylbutyrate; and (4) deprotection of the 4-hydroxy group. This route is tedious and gives low overall yields.

Simvastatin has also been prepared by the α-alkylation of the ester moiety as described in U.S. Pat. Nos. 4,582,915 and 4,820,850.

U.S. Pat No. 4,582,915 (1986) discloses the direct methylation of the natural 2-(S)-methylbutyryloxy side chain of mevinolin in a single chemical step using a metal alkyl amide and a methyl halide to give simvastatin. This process suffers from poor conversion rate of the C-methylation step. Additionally, many side reactions take place due to methylation at other sites of the molecule. The C-methylation conversion rate may be improved to some extent by a second or a third charge of the amide base and methyl halide. Even so, the overall yields are moderate. Also, the purity of simvastatin obtained by this process is close to borderline for use as a human health-care product.

U.S. Pat. No. 4,820,850 (1989) discloses a process wherein high conversion C-methylation of the 2-(S)-methylbutyryloxy side chain of mevinolin takes place with a single charge of amide base and alkyl halide. The process described in this patent comprises six steps and is not economical as it involves the protection and deprotection of the two hydroxy groups of the intermediate lovastatin butylamide using an expensive silylating agent, tert-butyldimethylsilyl chloride.

SUMMARY OF THE INVENTION

The present invention provides a novel process and novel intermediates for the preparation of simvastatin (IIa). The novel process may be depicted by the following reaction scheme:

REACTION SCHEME

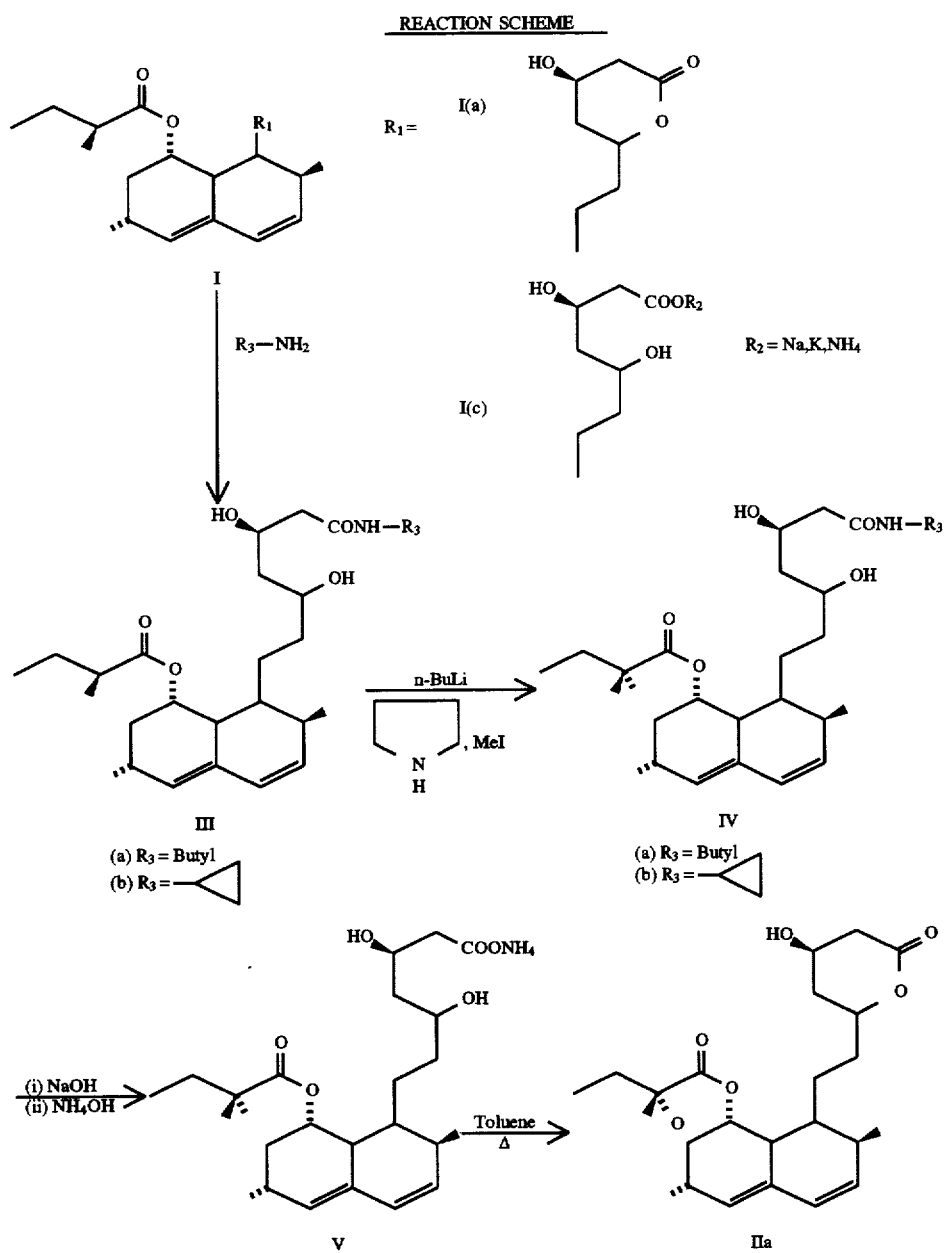

Salient features of the invention include:

(a) Simvastatin may be prepared from a salt of mevinolinic acid as the starting material rather than lovastatin.

(b) Simvastatin is prepared in a four step process which does not include the protection and deprotection of the two hydroxy groups of the open pyranone ring. Heretofore, the methods described in the prior art require the protection and deprotection of the hydroxy groups as essential steps for the preparation of simvastatin.

(c) In a preferred embodiment, the novel intermediate lovastatin cyclopropyl amide (IIIb) is prepared from the starting material (lovastatin or a salt form of mevinolinic acid). This novel intermediate is then converted into a second novel intermediate (IVb).

Simvastatin prepared by the inventive process has certain advantages in commercial manufacture. The purity and yield of simvastatin from the inventive process is high, with less consumption of reagents, time, labor, and cost, and in fewer steps.

DETAILED DESCRIPTION OF THE INVENTION

The starting material for the method of the present invention is lovastatin (Ia) or mevinolinic acid (Ic), the latter being the open ring form of lovastatin. Mevinolinic acid is produced by fermentation of *Aspergillus terreus* (see U.S. Pat. No. 4,231,938). Either lovastatin (Ia) or the salt form of mevinolinic acid (Ic) will typically be employed as the starting material. The term "mevinolinic acid" unless otherwise specified includes suitable salt forms thereof; any salt which will not interfere with other reagents or conditions used in carrying out the present invention is permissible. The alkali metal salts, e.g., Na and K, or, preferably, the ammonium salt form, may be employed.

Lovastatin is obtained from mevinolinic acid via lactonization by methods known in the art, and is isolated by loss incurring crystallization techniques. There is ca. 20% material loss in converting naturally occurring mevinolinic acid to lovastatin. One objective of this invention is to eliminate this loss by employing mevinolinic acid as the starting material rather than lovastatin.

According to the novel process of the present invention, simvastatin (IIa) is prepared by reacting lovastatin (Ia) or mevinolinic acid (Ic), preferably in the ammonium salt form, with an n-alklyamine or a cycloalkylamine of formula $R_3$—$NH_2$, wherein $R_3$ is $C_3$-$C_6$. Preferably, the amine $R_3$—$NH_2$ is cyclopropylamine and the intermediate that is formed is lovastatin cyclopropylamide (IIIb). Alternatively, the amine $R_3$—$NH_2$ is n-butylamine and the intermediate that is formed is lovastatin n-butylamide (IIIa).

The cyclic intermediate amide IIIa or IIIb thus prepared is dissolved in dry tetrahydrofuran and is added to a solution of alkali metal amide, e.g., lithium pyrrolidide in THF at a temperature of about −35° C. to −40° C. Lithium pyrrolidide is generated in situ by the reaction of n-BuLi with pyrrolidine in THF. The solution of intermediate amide IIIa or IIIb, and the in situ generated base is aged at about −35° to −40° C. for 1 hour, and dried alkyl halide, preferably methyl iodide (2 to 3.5 mol. eq.), is added in a single charge. The contents are stirred at about −30° C. for 1 hour, warmed to −10° C. and aged at this temperature for 20 minutes. Water is added to the reaction mixture and the layers are separated. The THF layer is washed with a mineral acid, preferably hydrochloric acid, and then concentrated to an oily mass which contains the intermediate IVa or IVb.

To the solution of intermediate IVa or IVb in methanol, without purification, is added 2.0N NaOH and is refluxed at about 80° to 81° C. for 2 to 6 hours, preferably for 2 hours. The mixture is cooled to about 50° C., and the methanol is stripped off at reduced pressure and then diluted with water. The mixture is then acidified at about 10° C. by careful addition of 2.0N HCl maintaining a pH of 6, extracted with ethyl acetate, while further acidifying to a pH of 4. The ethyl acetate layer is separated and the hydrolyzed product is precipitated out as a crystalline material in the form of ammonium salt (V) by slow addition of methanolic ammonium hydroxide over a period of 30 minutes at about 22°–25° C., followed by cooling to 5° C.

The ammonium salt (V) is relactonized by heating in a hydrocarbon solvent such as toluene. The mixture is suspended in toluene, heated and stirred at about 100°–110° C. for 2 to 10 hours, preferably at about 105° for 5 hours, under a sweep of nitrogen gas. The mixture is then cooled to about 35° C., carbon treated, filtered, and the filtrate is concentrated under reduced pressure at about a 60° C. bath temperature to one-tenth of its original volume. The lactone is crystallized from a hydrocarbon solvent such as cyclohexane to give simvastatin (IIa) of high purity.

In a most preferred embodiment of the novel process of this invention, mevinolinic acid (Ic) in its ammonium salt form is used as the starting material and is converted into lovastatin cyclopropylamide (IIIb). The mevinolinic acid salt is suspended in toluene and refluxed for 5–6 hours at about 100°–110° C., preferably at about 105°–107° C. The resulting solution is concentrated to one tenth of its volume by distilling the toluene at reduced pressure at about 50°–55° C. bath temperature. Cyclopropylamine is added at 30° C. and the mixture again heated for 4–5 hours at about 40°–50° C. Toluene and unreacted cyclopropylamine are distilled off at reduced pressure to afford lovastatin cyclopropylamide (IIIb) in quantitative yield. The cyclic amide thus prepared is used as such without purification in the next step of C-methylation in a similar way as described above without the protection of the dihydroxy system to give simvastatin (IIa).

The following examples further illustrate the present invention:

EXAMPLE I

Preparation of Simvastatin (IIa) from Mevinolinic Acid Ammonium Salt (Ib) Using Cyclopropylamine Step 1: N-Cyclopropyl-7-[1,2,6,7,8,8a(R)-hexahydro-2 (S), 6(R) -dimethyl-8(S)-[[2(S)-methylbutanoyl]oxy]-1 (S)-naphthyl]-3(R),5(R)-dihydroxyheptanoic acid amide (IIIb)

Mevinolinic acid ammonium salt (Ic) (12.5 g, 0.296 moles) was suspended in toluene (400 ml). The mixture was heated and stirred at 105°–107° C. under a sweep of nitrogen gas for 5 hours. The temperature was lowered to 60° C. and about 350 ml of toluene was distilled off. Cyclopropylamine (12 ml, 0.172 moles) was added at 30° C. and the solution was again stirred at 40°–45° C. for 4 hours. The toluene was slowly stripped off at reduced pressure and at a bath temperature of 55° C. to afford the title compound in gum-like form. HPLC purity=99.63%; $^1$H NMR (CDCl$_3$, 300 MHz): δ 0.495 (m, 2H), δ 0.50 (m, 2H), δ 0.86 (m, 6H), δ 1.08 (m, 6H), δ 2.3 (d, 2H), δ 2.6 (m,1H), δ 3.7 (m, 1H), δ 4.18 (m, 1H), δ 5.4 (m, 1H), δ 5.5 (bt, J=3.0 Hz, 1H), δ 5.7 (dd, J=6.1, 9.5 Hz, 1H), δ 5.9 (d, J=9.6 Hz, 1H), δ 6.2 (bt, J=5.3 Hz, 1H); IR(CHCl$_3$): λ max 3500–3300 (b), 3000, 1740, 1660, 1530, 1450, 1210, 860, 760 cm$^{-1}$.

This gum was directly used in the next step without purification.

Step-2: N-Cyclopropyl-7-[1,2,6,7,8,8a(R)-hexahydro-2 (S), 6(R)-dimethyl-8(S)-[[2,2-dimethyl-butanoyl]oxy]-1(S)-naphthyl]-3(R),5(R)-dihydroxyheptanoic acid amide (IVb)

Pyrrolidine (13.5 ml, 0.163 moles) in THF (50 ml) was cooled to −45° C. and n-butyl lithium in hexane (1.6M, 100 ml, 0.163 moles) was added under nitrogen at such a rate so as to maintain a temperature of −20° to −15° C. The mixture was stirred at −20° to −25° C. for 40 minutes after the completion of addition.

A solution of compound IIIb in THF (300 ml) was prepared as described above and then slowly added via a cannula maintaining the temperature below −35° C. during the whole addition. The solution was aged at −35° to −40° C. for 1 hour. Sieve dried methyl iodide (4.82 ml, 0.077 moles) was added in a single lot. The off-white, cloudy solution thus obtained was stirred for 1 hour at −35° to −33° C., then warmed to −10° C. and aged for 20 minutes. Distilled water (105 ml) was added to the reaction mixture and the contents vigorously stirred for 5 minutes. The layers were separated and the upper THF layer was treated with 1N HCl (105 ml). The THF layer was concentrated at reduced pressure to a volume of about 40 ml to yield the title compound IVb, wherein $R_3$ is cyclopropyl.

Step-3: 6(R)-[2-[8(S)-(2,2-dimethylbutyryloxy)-2(S),6 (R)-dimethyl-1,2,6,7,8,8a(R)-hexahydro-1(S)-naphthyl]ethyl]-4(R) -hydroxy-3,4,5,6-tetrahydro-2H-pyran-2-one (IIa) (Simvastatin)

To the concentrated solution from the previous step containing compound IVb was added an aqueous solution of NaOH (2N, 25 ml) and MeOH (175 ml). The mixture was refluxed at 80°–81° C. for 2 hours. The mixture was cooled to 50° C., maximum MeOH was stripped off at reduced pressure, and diluted with water (90 ml). Acidification of the solution was done at 10° C. by careful addition of 2N HCl (pH 6). Ethyl acetate (200 ml) was added and the mixture was vigorously agitated while further acidifying to pH of 4. The ethyl acetate layer was separated from the aqueous one. A solution of NH$_4$OH and MeOH (1:1, 10 ml) was slowly added in over 30 minutes at 22°–25° C. The precipitates were stirred at 25° C. for 1.5 hour, cooled to 5° C. and stirred at this temperature for 30 minutes. Filtration followed by washing with cold ethyl acetate (25 ml) and drying in vacuum at 35° C. afforded the ammonium salt (V).

The crude ammonium salt (V) from the previous step (10 g, 0.022 moles) was suspended in toluene (350 ml). The mixture was heated and stirred at 105° C. under a sweep of nitrogen for 5 hours. The solution was cooled at 35° C., activated charcoal (0.5 g) was added, stirred for 0.35 hour, and then filtered through celite bed. The filtrate was concentrated in vacuum to a volume of 40 ml at 60° C. bath temperature. Cyclohexane (125 ml) was added and the solution again refluxed for 15 minutes, cooled for 1 hour to 25° C., and further cooled to 10°–12° C. for 30 minutes. The precipitates were stirred at 10°–12° C. for 30 minutes, filtered and washed with cold cyclohexane (50 ml), dried in vacuum at 35° C. to give white crystalline product (IIa) which was further crystallized from absolute ethanol to afford the title product of >99% purity.

EXAMPLE II

Preparation of Simvastatin (IIa) from Lovastatin (Ia) Using Cyclopropylamine

Step-1: N-Cyclopropyl-7-[1,2,6,7,8,8a(R)-hexahydro-2 (S), 6(R)-dimethyl-8)S)-[2(S)-methylbutanoyl]oxy]-1 (S)-naphthyl]-3(R),5(R)-dihydroxyheptanoic acid amide (IIIb)

Lovastatin (Ia) (12.5 g, 0.03 moles) was suspended in cyclopropylamine (13 ml, 0.174 moles) at 25° C. The mixture was slowly heated to 40°–45° C. and stirred at this temperature for 5 hours. Excess amine was evaporated off at reduced pressure and a 40° C. bath temperature to afford the title compound in gum-like form. This gum was directly used in the next step without purification.

Steps 2-3: Compound (IIIb) obtained from the previous step was converted into simvastatin (IIa) by following the same procedure as described for Example I.

EXAMPLES III and IV

Preparation of Simvastatin (IIa) from Lovastatin (Ia) and Mevinolinic Acid Ammonium Salt (Ic) Using n-Butylamine Simvastatin (IIa) was prepared from lovastatin (Ia) and mevinolinic acid ammonium salt (Ic) as starting materials following the same steps as described in Examples I and II but substituting equimolar quantities of n-butylamine in place of cyclopropylamine.

While the invention has been described by reference to specific embodiments, this was for purposes of illustration only. Numerous alternative embodiments will be apparent to those skilled in the art and are considered to be within the scope of the claims.

We claim:
1. A process for producing a compound of structural formula IIa:

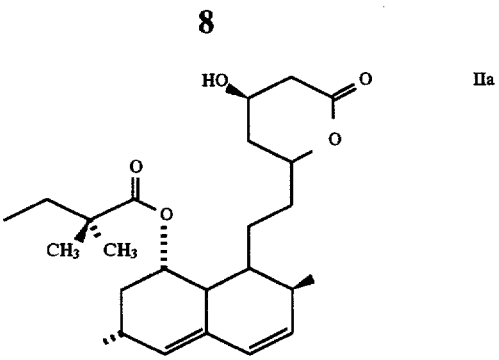

comprising:

(i) treating a compound of structural formula I':

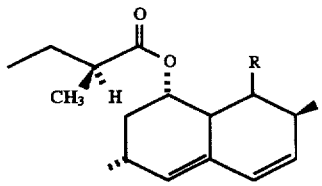

wherein R is:

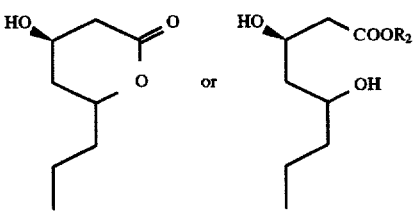

and R$_2$ is H, Na, K or NH$_4$, with an alkyl amine having the formula R$_3$NH$_2$, wherein R$_3$ is a C$_3$–C$_6$ n-alkyl or cycloalkyl group, to produce a compound of structural formula III:

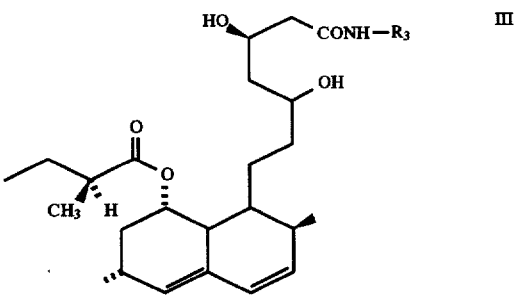

(ii) treating said compound of structural formula III with a methylating agent to produce a compound of structural formula IV:

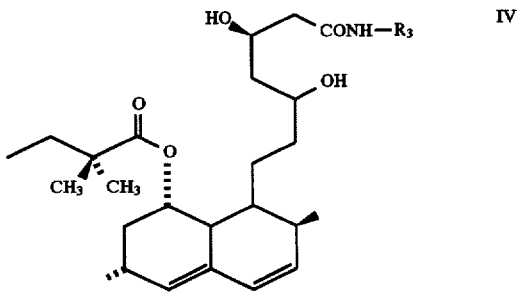

wherein R$_3$ is as defined above;

(iii) hydrolyzing the amide linkage and closing the open pyranone ring of said compound of structural formula IV to produce said compound of structural formula IIa.

2. The process of claim 1 wherein step (ii) is performed without protecting or deprotecting the two hydroxy groups of the open pyranone ring of said compound of structural formula III.

3. The process of claim 1 wherein step (iii) is performed by treating said compound of structural formula IV with a base to hydrolyze the amide linkage and thereafter heating the resulting compound in an organic solvent to produce said compound of structure formula IIa.

4. The process of claim 3 wherein the $R_3$ group is cleaved by treating said compound of structural formula IV with a strong base followed by treatment with ammonium hydroxide to produce a compound of structural formula V:

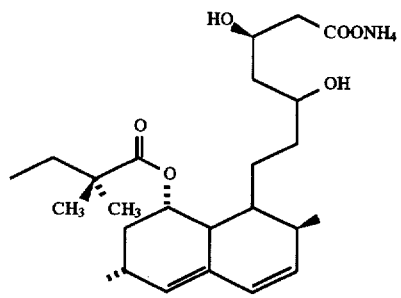

5. The process of claim 4 wherein said strong base is sodium hydroxide.

6. The process of claim 3 wherein said organic solvent is toluene.

7. The process of claim 1 wherein $R_3$ is a cyclopropyl group.

8. The process of claim 1 wherein $R_3$ is a n-butyl group.

9. The process of claim 1 wherein said methylating agent is methyl halide.

10. The process of claim 9 wherein said methylating agent is methyl iodide.

11. The process of claim 9 wherein said compound of structural formula III is treated with said methyl halide in the presence of a base.

12. The process of claim 11 wherein said base is lithium pyrrolidide.

13. The process of claim 1 wherein $R_2$ is $NH_4$.

14. A process for producing a compound of structural formula IIa:

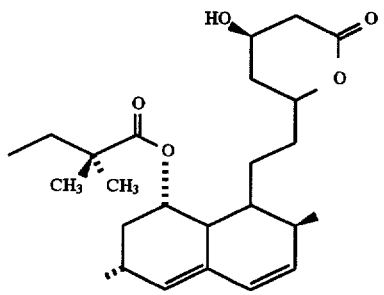

comprising:

(i) treating a compound of structural formula I':

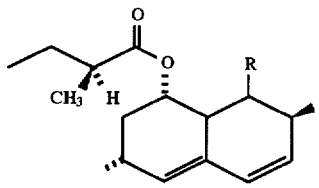

wherein R is:

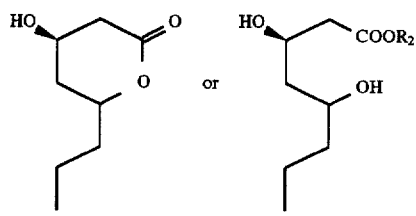

and $R_2$ is H, Na, K, or $NH_4$, with cyclopropyl amine to produce a compound of structural formula III;

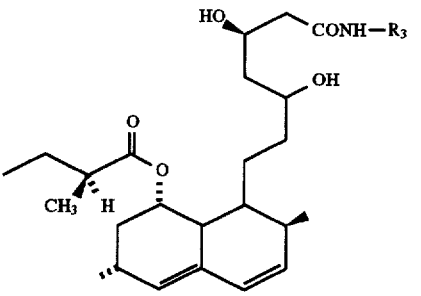

wherein $R_3$ is a cyclopropyl group;

(ii) treating said compound of structural formula III with methyl halide to produce a compound of structural formula IV:

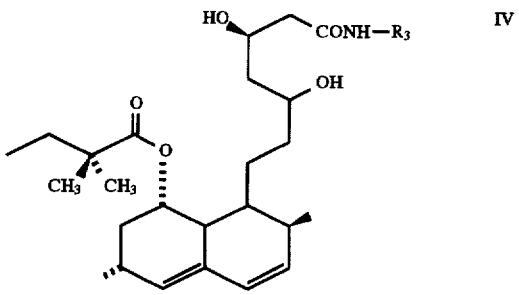

wherein $R_3$ is as defined above;

(iii) hydrolyzing the amide linkage and closing the open pyranone ring of the compound of structural formula IV to produce said compound of structural formula IIa.

15. The process of claim 14 wherein $R_2$ is $NH_4$.

16. The process of claim 14 wherein said methyl halide is methyl iodide.

17. The process of claim 16 wherein said compound of structural formula III is treated with methyl iodide in the presence of lithium pyrrolidide.

18. The process of claim 14 wherein step (iii) is carried out by treating said compound of structural formula IV with a base followed by heating in an organic solvent.

19. The process of claim 18 wherein said base comprises sodium hydroxide followed by ammonium hydroxide.

20. The process of claim 18 wherein said organic solvent is toluene.

21. A process for preparing a compound of structural formula III:

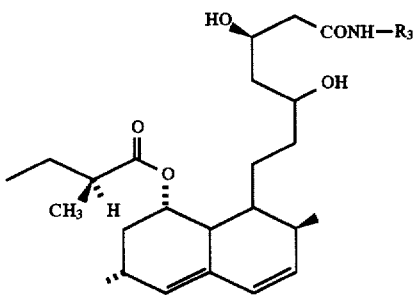 III wherein $R_3$ is cyclopropyl, comprising treating a compound of structural formula I':

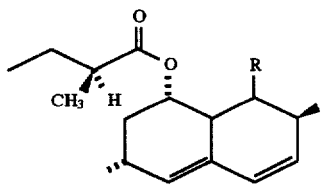 I' wherein R is:

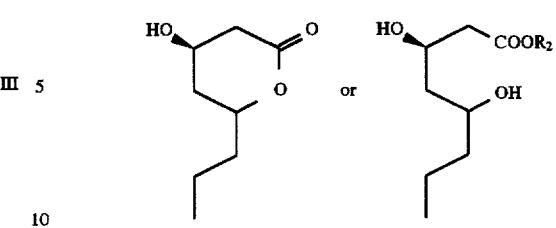

and $R_2$ is Na, K, or $NH_4$, with cyclopropyl amine.

22. The process of claim 21 wherein $R_2$ is $NH_4$.

23. The process of claim 21 further comprising methylating the methylbutyrate side chain of the compound of structural formula III without protecting or deprotecting the hydroxy groups to produce a compound of structural formula IV:

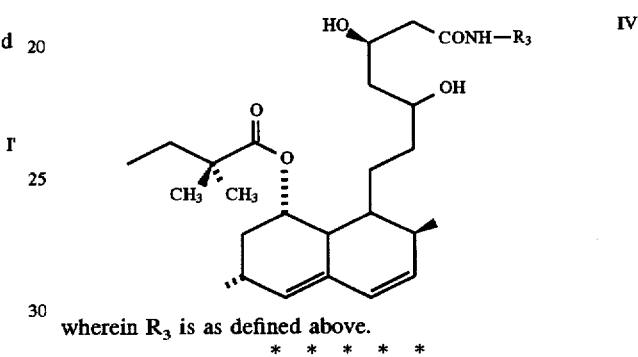 IV wherein $R_3$ is as defined above.

* * * * *